(12) United States Patent
Skoglund

(10) Patent No.: US 7,880,142 B2
(45) Date of Patent: Feb. 1, 2011

(54) EXTENDED ELECTRON TOMOGRAPHY

(75) Inventor: Ulf Skoglund, Stockholm (SE)

(73) Assignee: Sidec Technologies AB, Kista (SE)

( * ) Notice: Subject to any disclaimer, the term of this patent is extended or adjusted under 35 U.S.C. 154(b) by 291 days.

(21) Appl. No.: 12/296,237

(22) PCT Filed: Apr. 4, 2007

(86) PCT No.: PCT/SE2007/000324

§ 371 (c)(1),
(2), (4) Date: Oct. 6, 2008

(87) PCT Pub. No.: WO2007/114772

PCT Pub. Date: Oct. 11, 2007

(65) Prior Publication Data

US 2009/0283676 A1   Nov. 19, 2009

Related U.S. Application Data

(60) Provisional application No. 60/788,699, filed on Apr. 4, 2006.

(51) Int. Cl.
*H01J 37/26* (2006.01)
(52) U.S. Cl. .................. 250/307; 250/306; 250/311
(58) Field of Classification Search .................. 250/307, 250/306, 311, 310
See application file for complete search history.

(56) References Cited

U.S. PATENT DOCUMENTS 7,154,091 B2 * 12/2006 Zewail et al. ............... 250/311

2006/0120579 A1 * 6/2006 Skoglund et al. ............ 382/128
2006/0261269 A1 * 11/2006 Skoglund ................... 250/311

FOREIGN PATENT DOCUMENTS

| WO | WO 9733255 | 9/1997 |
| WO | WO 2004006189 | 1/2004 |
| WO | WO 2004068415 | 8/2004 |

OTHER PUBLICATIONS

Haixiao Gao, et al., "Dynamics of EF-G interaction with the ribosome explored by classification of a heterogeneous cryo-EM dataset", Journal of Structural Biology, 147 (2004), pp. 283-290.
M. van Heel, et al., "Angular Reconstitution in Three-Dimensional Electron Microscopy: Historical and Theoretical Aspects", Scanning Microscopy, vol. 11, 1997, pp. 195-210.
International Search Report dated Jul. 19, 2007, in PCT application.

* cited by examiner

*Primary Examiner*—Kiet T Nguyen
(74) *Attorney, Agent, or Firm*—Young & Thompson

(57) ABSTRACT

A method for improving image resolution of a three dimensional structure of at least one molecule conformation includes: determining a three dimensional structure of at least one conformation of a molecule in a sample from a first data set obtained from a series of 2D measurements of different geometrical projections of the molecule at a low electron beam dose in an electron microscope; producing a second data set including calculated two dimensional projections of the determined three dimensional structure of the at least one conformation of the same molecule; correlating data from a third data set obtained from at least one measurement of the same molecule using a higher electron beam dose with the second data set; and using the correlated data to improve the resolution of the three dimensional structure of the at least one conformation of the molecule by increasing the first data set with the correlated data and re-determining a three dimensional structure.

16 Claims, 11 Drawing Sheets

Tilt -60° (low-dose tilt series)　　Without noise (not used)

Tilt 0° (low-dose tilt series)　　Without noise (not used)

Tilt +60° (low-dose tilt series)　　Without noise (not used)

A

B

EXTENDED ELECTRON TOMOGRAPHY

TECHNICAL FIELD

The present invention relates to electron tomography in an electron microscope and in particular to a method, computer program, and electron microscope using at least one experimentally determined three dimensional conformation as a tool for selecting and orienting particles from 2D EM images for improving the 3D conformation image resolution.

BACKGROUND OF THE INVENTION

Today cryo electron microscopy can be used to determine the 3 dimensional structures of macromolecules at near atomic resolution. EM can be used to get diffraction from 2D crystals or images in 2D of macromolecules that can be reconstructed into 3D by using 2D images from different angles. The first method is usually referred to as EM crystallography and the latter can be divided into electron tomography and single-particle electron microscopy. The electron tomography approach requires many pictures of the same particle tilted into different orientations. The single particle technique, collect 2D images of objects without tilting the specimen. The method exploits random orientations that particles assume in vitrified solvent to extract 3D information. A difference between the two methods is that when the specimen is tilted, 3D reconstructions of objects represent a single object in contrast to when using zero-tilt images the 3D reconstructed object represents an average of similar objects.

When the specimen is tilted, the relationship between the images and therefore the objects in the images are known by the tilt angle making the reconstruction of the object relatively straightforward. For zero-tilt techniques the relationship between the images and the objects in the images are unknown which leads to difficulties in relating the different objects to each other. A second complication for zero tilt techniques is that macromolecules are dynamic so that the objects in the images represent different conformations of the molecules. This adds another difficulty in the 3D reconstruction of macromolecules from zero tilt series data sets.

A major problem with the zero-tilt technique is to infer the orientations of the particles in the 2D images to enable a 3D structure to be determined. A number of techniques have been developed for an overview see (Angular Reconstitution in Three-Dimensional Electron Microscopy Historical and Theoretical Aspects, Scanning Microscopy Vol. 11 1997:195-210). None of the techniques that have been developed uses experimental information to establish the relationship between 2D images of random orientation. Structures without internal symmetry have been determined at resolutions of 5-9 Å, using zero tilt techniques.

Another major problem with the zero tilt techniques is that knowledge is lacking about how the macromolecules look in 3D before the molecular objects are oriented and reconstructed. As proteins are dynamic it is expected that the 2D molecular images represents different conformations of the molecule (sometimes referred to as conformers), and therefore there is a big risk that the 3D reconstructed objects will originate from 2D molecular images of different conformations, which will limit the resolution that can be achieved. This has been recognized by Gao et al, (Dynamics of EF-G interaction with the ribosome explored by classification of a heterogeneous cryo-EM dataset. J of Struct. Biol. 147, 2004, 283-290) where known differences have been used to make sub selections of molecular images that was used for reconstructions.

There is a need for a tool that enables the orientation of different conformations of a macromolecule so that the 3D reconstruction from 2D zero tilt images only contain images representing one single conformation.

SUMMARY OF THE INVENTION

The object of the present invention is to provide such a tool that remedies some of the above mentioned problems This is done in a number of aspects wherein a first aspect, a method for improving the image resolution of a three dimensional structure of at least one molecule conformation is provided, comprising the steps of:

determining a three dimensional structure of at least one conformation of a molecule in a sample from a first data set obtained from a series of 2D measurements of different geometrical projections of the molecule at a low electron beam dose in an electron microscope;

producing a second data set comprising calculated two dimensional projections of the determined three dimensional structure of the at least one conformation of the same molecule;

correlating data from a third data set obtained from at least one measurement of the same molecule in an electron microscope using a higher electron beam dose with the second data set; and using the correlated data to improve the resolution of the three dimensional structure of the at least one conformation of the molecule by increasing the first data set with the correlated data and re-determining a three dimensional structure.

The low dose electron beam may be below a damaging level for the molecule conformation.

The low dose electron beam may be below 1 $e^-/Å^2$ per image.

The higher dose electron beam may be higher than 1 $e^-/Å^2$ per image.

The step of determining a three dimensional structure may comprise a step of using a constrained maximum entropy tomography method.

The method may further comprise the step of producing a new second data set by simulating two dimensional projections of the improved three dimensional structure.

Another aspect of the present invention, a machine with a memory containing data representing a three dimensional structure obtained from the method defined above is provided.

Yet another aspect of the present invention, a computer program is provided for improving image resolution of a three dimensional structure of at least one conformation of a molecule comprising instruction sets for:

determining a three dimensional structure of at least one conformation of a molecule in a sample from a first data set obtained from a series of 2D measurements of different geometrical projections of the molecule at a low electron beam dose in an electron microscope;

producing a second data set comprising calculated two dimensional projections of the determined three dimensional structure of the at least one conformation of the same molecule;

correlating data from a data third data set obtained from at least one measurement in an electron microscope of the molecule using a higher electron beam dose with the second data set; and using the correlated data to improve the resolution of the three dimensional structure of the at least one conformation of the molecule by increasing the first data set with the correlated data and re-determining a three dimensional structure.

The computer program may further comprise an instruction set for producing a new second data set by calculating two dimensional views of the improved three dimensional structure.

Still in another aspect of the present invention, an electron microscope system is provided arranged with image analysis software for improving image resolution of a three dimensional structure of at least one conformation of the molecule comprising instruction sets for:
  determining a three dimensional structure of at least one conformation of a molecule in a sample from a first data set obtained from a series of 2D measurements of different geometrical projections of the molecule at a low electron beam dose in an electron microscope;
  producing a second data set comprising calculated two dimensional projections of the determined three dimensional structure of the at least one conformation of the same molecule;
  correlating data from a data third data set obtained from at least one measurement in an electron microscope of the molecule using a higher electron beam dose with the second data set; and
  using the correlated data to improve the resolution of the three dimensional structure of the at least one conformation of the molecule by increasing the first data set with the correlated data and re-determining a three dimensional structure.

The present invention may also be realized as a propagated signal comprising a data structure representing a three dimensional structure obtained from the method described above.

Another aspect of the present invention, a computer readable data medium is provided containing a data structure representing a three dimensional structure obtained from the method described above The computer readable data medium may be at least one of a hard disk, diskette, CD-ROM (Compact Disk-Read Only Memory), DVD (Digital Video Disk), flash or similar removable memory media (e.g. compact flash, SD secure digital, memorystick, miniSD, MMC multimediacard, smartmedia, transflash, XD), HD-DVD (High Definition DVD), or Bluray DVD, USB (Universal Serial Bus) based removable memory media, magnetic tape media, optical storage media, magneto-optical media, and bubble memory.

Yet another aspect of the present invention, an image is provided stored as a data structure in a computer readable medium representing a three dimensional structure obtained from the method described above.

These and other aspects of the invention will be apparent from and elucidated with reference to the embodiments described hereinafter.

BRIEF DESCRIPTION OF THE DRAWINGS

In the following the invention will be described in a non-limiting way and in more detail with reference to exemplary embodiments illustrated in the enclosed drawings, in which.

DETAILED DESCRIPTION OF PREFERRED EMBODIMENTS

The present invention combines the 2D (two dimensional) image information of individual molecules of interest taken with low dose electron microscopy from several directions, e.g. by tilting the sample and acquiring images in a tilt series, used for determining the three dimensional structure, with image information in 2D taken at higher dose electron microscopy. The two image information sets may be correlated to each other and used in improving the 3D image information from the 2D set. The 3D "experimentally determined" structures of the molecule using low dose electron microscopy are used to provide simulated views of different conformations of the molecular structures. The simulation is provided with different angles of view of the molecule, different electron beam dosage, different molecules of interest, and so on. These simulated conformations are used in the determination of conformations present in the 2D image material.

Figure 1:
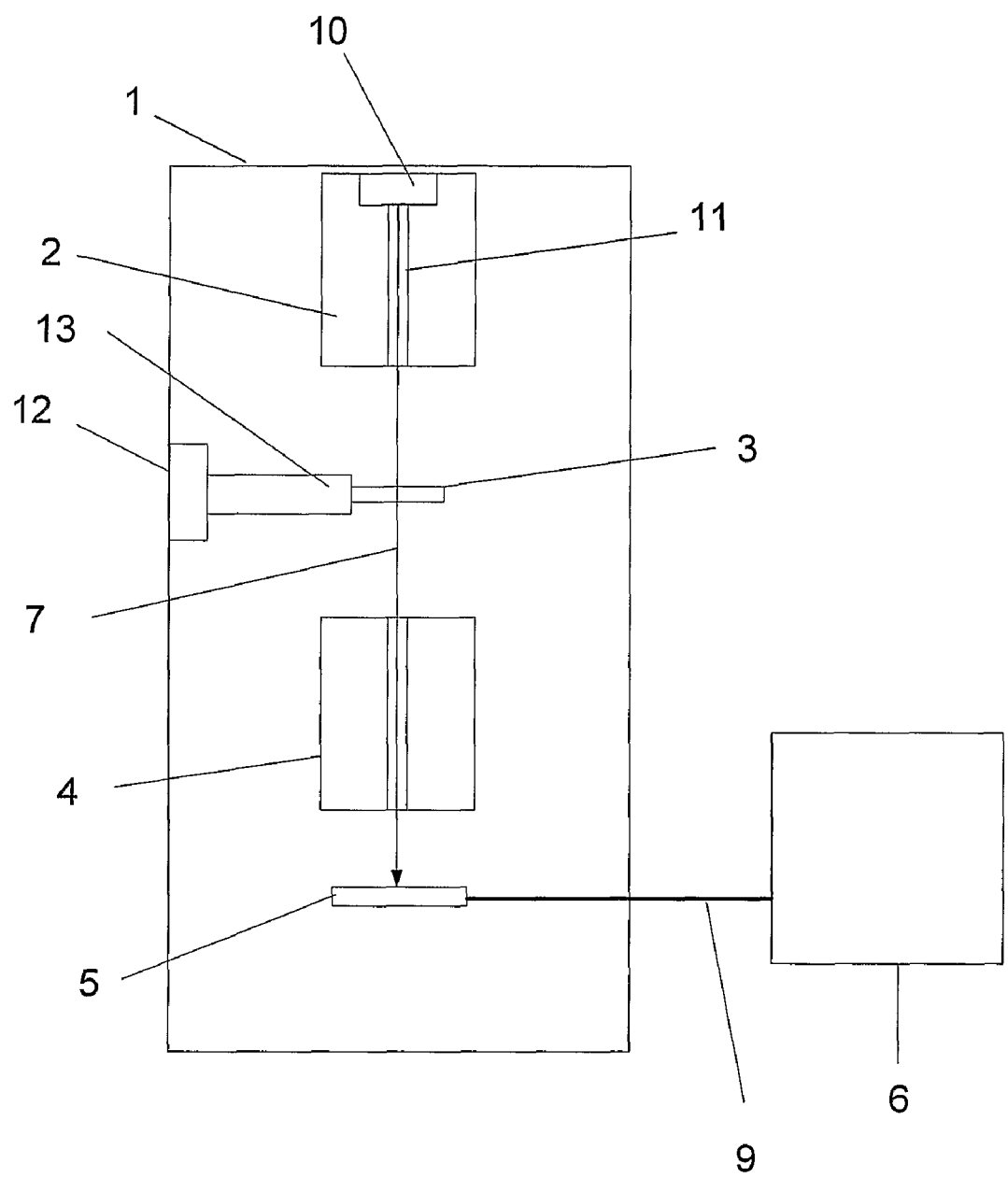
FIG. 1 illustrates schematically an electron microscope setup used in the present invention.

In FIG. 1 reference numeral 1 generally denotes an electron microscope system comprising an electron beam 7 generator 10 and a first electron beam lens 2 with an electron beam passage 11. The microscope 1 further comprise a second electron beam lens 4 located below a sample 3 to be tested with a similar electron beam passage. The electron beam 7 will be detected by an image acquisition device 5, e.g. a CCD (Charge Coupled Device) or similar image detecting device connected 9 to a processing device 6. Data from the image acquisition device 5 is transmitted to the processing device 6 that also may be arranged to control the configuration and operation of the electron microscope 1. The electron microscope may comprise other parts as well but these are not shown explicitly since they are know to the person skilled in the art and also depend on what type of microscope and configuration of the microscope 1. The setup shown in FIG. 1 is for a transmission electron microscope 1. The electron microscope generates an electron beam using the electron beam generator 10, the first lens forms an electron beam shape desired depending on experimental situation. In case of a transmission electron microscope the electron beam 7 passes through the sample 3 and interacts with the sample 3. The second electron lens 4 may be used optionally for controlling the shape and/or direction of the electron beam after the interaction with the sample 3; it may also be used for decreasing any effects of external or internal noise. The electron beam 7 is finally collected in the image acquisition device 5 for digitization and immediate or later digital analysis in the processing device 6 or elsewhere.

Figure 2:
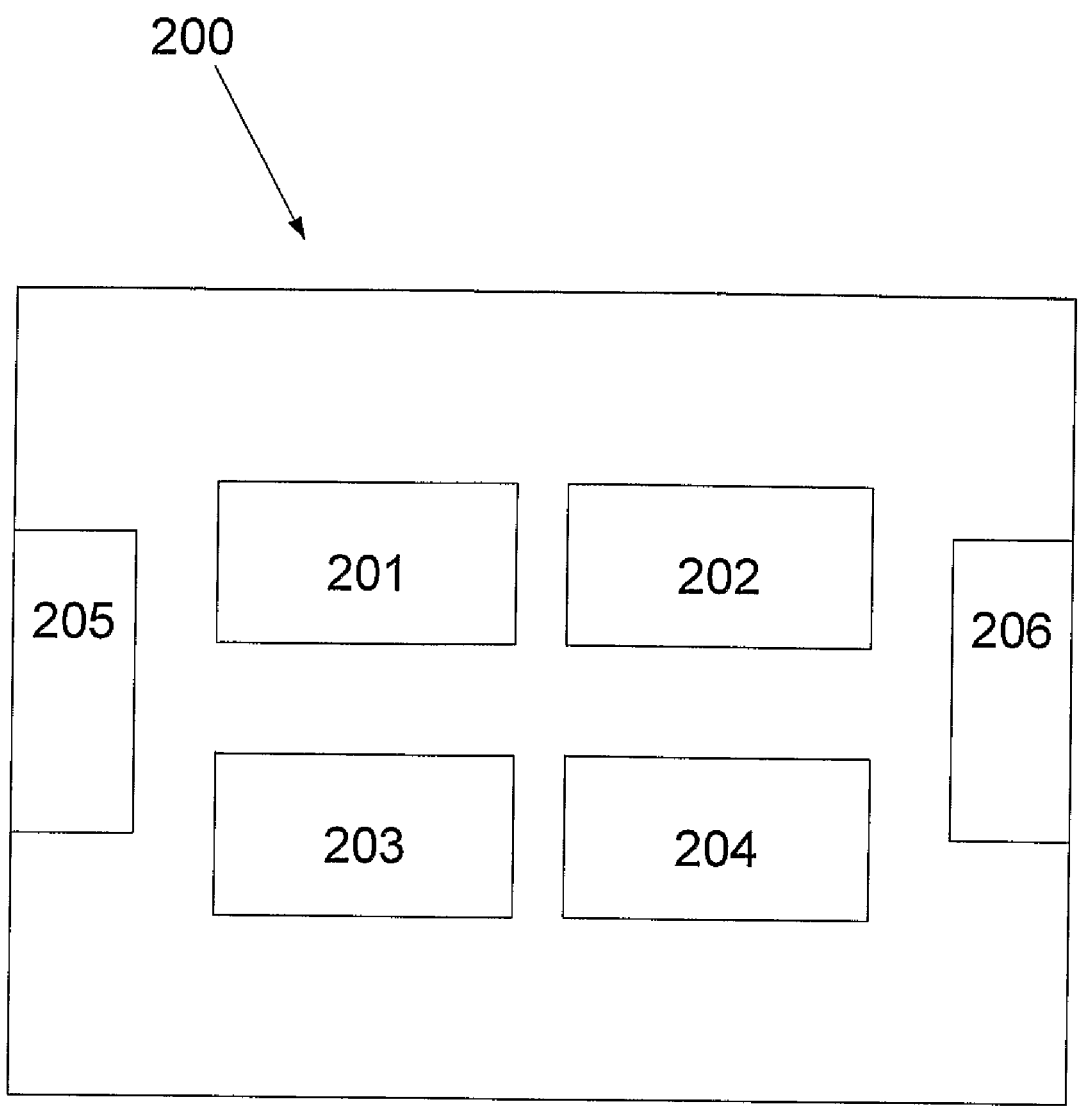
FIG. 2 illustrates schematically a processing device according to the present invention.

The processing device 6, 200 is shown in detail in FIG. 2, wherein a processing unit 201 handles image analysis and interaction with the microscope and user. The processing device 200 further comprises a volatile (e.g. RAM) 202 and/or non volatile memory (e.g. a hard disk or flash disk) 203, an interface unit 204. The processing device 200 may further comprise a data acquisition unit 205 and communication unit 206, each with a respective connecting interface. All units in the processing device can communicate with each other directly or indirectly through the processing unit 201. The processing unit 201 processes data, controls data acquisition, and handles interface commands using appropriate software, data and analysis results may be stored in the memory unit(s) 202, 203. The interface unit 204 interacts with interface equipment (not shown), such as input devices (e.g. keyboard and mouse) and display devices. The data acquisition unit 205 interacts with the electron microscope 1 and receives data from the image acquisition device 5. The communication unit 206 communicates with other devices via for instance a network (e.g. Ethernet). Image data can also be stored and analyzed later in the processing device 200 or in any other suitable processing device, e.g. a server, personal computer or workstation. The analysis method according to the present invention is usually realized as computer software stored in the memory 202, 203 and run in the processing unit 201. The analysis software can be implemented as a computer program product and distributed on a removable computer readable media, e.g. diskette, CD-ROM (Compact Disk-Read Only Memory), DVD (Digital Video Disk), flash or similar removable memory media (e.g. compactflash, SD secure digital, memorystick, miniSD, MMC multimediacard, smartmedia, transflash, XD), HD-DVD (High Definition DVD), or Bluray DVD, USB (Universal Serial Bus) based removable memory media, magnetic tape media, optical storage media, magneto-optical media, bubble memory, or distributed as a propagated signal via a computer network (e.g. Internet, a Local Area Network (LAN), or similar networks). The same type of media may be used for distributing results from the measurements of the electron microscope for post analysis at some other computational/processing device.

Samples may be prepared according to any electron microscopy suitable technique depending on the molecules to be detected and structure determined as understood by the person skilled in the art, for instance by cryo sectioning of biological material or depositing of thin films on a suitable substrate.

The electron microscope 1 is arranged with an intake port 12 for entering a sample to study into the electron microscope 1. The sample may be arranged on a sample holder 13 provided with means for tilting (e.g. a mechanical tilting arrangement) or other means for changing the geometrical position of the sample with respect to the incident electron beam. While exposing the sample to an average low dose (in the range of 0.15 $e^-/Å^2$, e.g. from 0.01 to 1 $e^-/Å^2$ per image) a series of 2D images at different tilt angles or different perspective views may be acquired and stored. The dose is preferably but not necessarily chosen such as to be below a damaging level for the molecule of interest; often damage is induced if the total electron beam dose is of the order of 30-40 $e^-/Å^2$ in total (however this is dependent on type of molecule and acceleration voltage of the electron microscope). The number of images acquired in this type of tilt series may be of the order 121 images taken each with one degree difference from each other from −60 to +60 degrees tilt angle for instance. It should be understood that any number of images can be acquired, using smaller tilt change increments. However, depending on the desired resolution of the determined three dimensional structure in the final result one may of course allow some damage to the molecules under inspection, i.e. increase the electron beam dosage in order to acquire images with higher quality while allowing some damage to the molecules with some degradation in the final resulting image.

Different molecules and/or conformations of the same molecule present in the images may be identified and analyzed into a three dimensional representation of the molecule or molecules. Constrained maximum entropy tomography methodology may be used for forming the three dimensional images of the different molecules resulting in a data set 3D (1 . . . N). The constrained maximum entropy tomography method has been described earlier, for instance in U.S. Pat. No. 6,418,243 which is incorporated herein by reference. Simulation software may be used to generate a number of 2D synthetic representations of each identified molecule from different view points (projections), P3D (1 . . . N), to be used in later analysis as described below. Also different synthetic representations may be produced by varying different other parameters, such as contrast transfer function (CTF), noise, electron dose and so on. Many transmission electron microscopes have an optional sample holder that has above described tilting arrangement; however, other standard or non standard sample holders may be used for changing how the electron beam strikes the sample and thus different geometrical views may be acquired. In another embodiment of the present invention the sample is contained in a tube and made to move in a spiral pattern while being exposed to the electron beam.

The same sample or a different sample containing similar molecules of interest as in the low dose experiment may be exposed to a higher dose of electron beam (in the range of 10 $e^-/Å^2$, e.g. 1 $e^-/Å^2$ and upwards per image) and one or several images may be acquired without any tilting operation; resulting in a data set M of K particles in different conformational views (k1, k2, k3, . . . , kM). The dose may be below or above the damaging level for the particular molecule as long as the resulting images contains data about the undamaged molecule. Often the damaging level is of the order >30-40 $e^-/Å^2$ and thus with 10 $e^-/Å^2$ per image a total of 3 to 4 images can be obtained without damaging the sample. These un-tilted (2D) images may be examined using an algorithm for detecting and identifying structures, for instance an algorithm based on constrained maximum entropy tomography methodology (COMET). However, the invention is not limited to COMET but other methods may be used. Both iterative and/or non-iterative methods may be used during this step: e.g. a non-iterative method such as filtered back projection or an iterative method such as COMET.

The detected and identified 2D images of the structures M are sorted and correlated according to the synthetic representations. This will provide an extended data set for determining the three dimensional structure of the molecule(s) of interest. The extended data set may be used for increasing the resolution of the three dimensional structure, for instance using constrained maximum entropy tomography methodology.

With this improved resolution of the three dimensional structure it is possible to simulate new synthetic views used for correlation with the 2D data set in turn used for providing yet more extended data set for use in increasing the resolution further and so on. As long as the resolution improves the iterative process may continue. A user of the method may provide a stop criterion that is relevant depending on type of molecule or other configurations of importance for the user.

Figure 3:
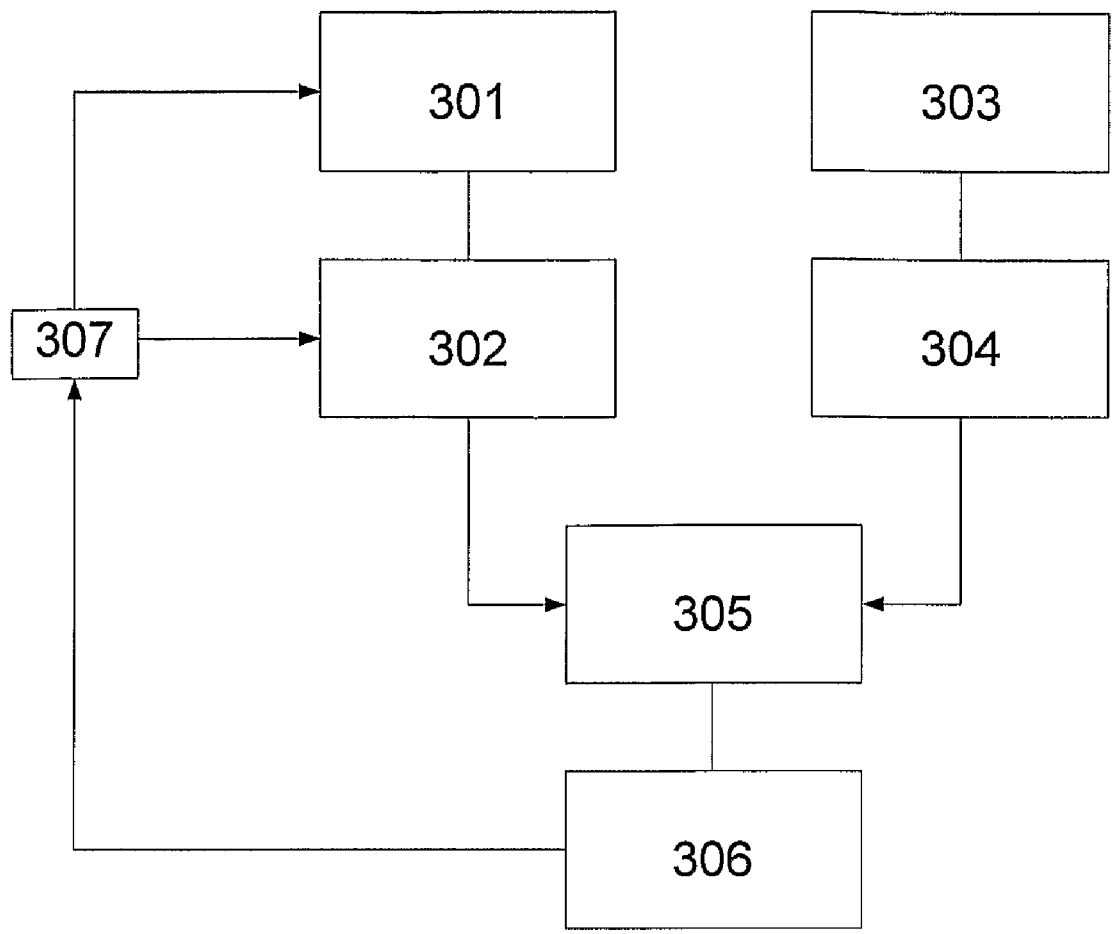
FIG. 3 illustrates schematically in a box diagram a method according to the present invention.

The method is illustrated schematically in FIG. 3 as a block diagram. In the first step 301 the tilt series of 2D images using a low dose electron beam is acquired and 3D structures of different molecules or conformations of a molecule are determined. In the second step 302 synthetic 2D views are calculated for the different conformations from the determined 3D structures. In step 303 the higher dose electron beam 2D images are acquired and in step 304 different molecules or conformations of a molecule are identified. In step 305 the 2D conformations obtained in step 303 are correlated with the synthetic views produced in step 302 and in step 306 the correlated conformations from the 2D data in step 305 are sorted with respect to the 3D structure data set determined in 301 and can be used for determining a new 3D data set; i.e. back to step 301. Optionally, it is possible to have a determination step 307 which may determine if the correlated 2D data set should be sent to step 301 or 302 depending on the obtained quality of the overall 3D structure data set or for an individual molecule or molecule conformation of interest. The method according to the present invention may be called AMET (Augmented Molecular Electron Tomography).

The method can be summarized in the following steps:
1) Collect Electron Tomography (EM) 2D images as a tilt series of a molecule.
2) Reconstruct a data set from the tilt series with a method capable of reconstructing individual molecules into 3D structures, e.g. using the COMET method
3) Classify the different objects into different conformations of the molecule.
4) Synthetic 2D projections for all conformations are calculated (with different CTF) from the reconstructed 3D structures in 2).
5) Collect 2D high dose images
6) Correlate the 2D high dose images obtained in 5) with the synthetic projections calculated in 4).
7) Collect all "particles" in the 2D data set that belongs to a specific conformation
   a. As there exists experimental data of the particles from the original tomograms, simulations can be done to understand what correlation is needed for a specific object to belong to the different conformers
8) Re-run the reconstruction with the first data set and the selected data set
9) If the resolution improves for each object, the selected data belongs to the selected conformation.
10) Use the improved reconstructed objects to create improved re-projection as in 4 above and continue until no further improvements in resolution is obtained for the different conformers Or in a slightly different manner:
1. Obtain a number of 2D images of a molecule in a tilt series and reconstruct into 3D structures with e.g. COMET-refined 3D-reconstructions. Call these the 3D (1 ... N), note the dose of about 0.15 $e^-/Å^2$.

These 3D reconstructions will contain several structural conformations of the molecule of interest.

2. Collect M 2D images at high dose 10 $e^-/Å^2$ with a varying defocus on an in vitro sample solution of the molecule. On each image will be seen many projections of the molecule, maybe in different conformational states. Giving K particles (k1 k2 k3 ... kM).

This will be a reference sample of the molecule in at least 3 different states (orientation, focus and conformational state).

3. Using 3D (1 ... N); calculate for each 3D volume a data set containing for instance 20000 random but well known orientation projections. One may also consider varying the CTF. Call this P3D (1 ... N).

4. This is a ranking and sorting stage.

Correlate all the K (k1 k2 k3 ... kM) particles in data set M with the P3D (1 ... N) data set to obtain all reasonable matches. Sort the ranking for each molecule i in data set 3D (1 ... N). Thus for each observed molecule in a particular conformation there will now be a new, extended, set of projections coming from data set M. Or, vice versa, the projections from dataset M are now sorted as to which 3D conformer they belong.

5. Recalculate the 3D (i) volume whenever a sufficiently high number of new projections have been found. Check to see if the resolution is increased and that the correlation criterion used in step 4 has been sharp enough not to mix the conformers. One way to ensure the selection criterion is to use simulation software to generate projections that emulates the physical conditions during data collection (dose, focus, magnification etc) and then check what correlation number is needed for a particular conformer to be maintained after selection of the dataset.

6. At some point the data set in 1 is no longer needed for volume 3D(i). For instance when the extended data set new projections for a given conformation gives similar resolution without help of the original data set from the tilt series. An advantage of disconnecting the use of the original data set from the tilt series is that the optical parameters are better defined for the un-tilted data set.

7. Reiterate with updated 3D (i) volumes from step 3. Use a stop criterion to end the iteration for a specific volume. One stop criteria may be that recalculations do not give any higher resolution which can be measured for instance using a shell-correlation method by dividing the data set into two parts and comparing the similarity of the resolution for these two data sets. At near atomic resolution (or at atomic resolution) the shell-correlation method may be applied to fragmental structures and determine the resolution for these.

Some of the steps may be performed at different stages and the invention is not limited to the order of the steps as exemplified above. For instance the steps of acquiring low dose tilt series may be done after the higher dose 2D experimental data set. However, for samples sensitive to higher dosage electron beam there is a potential risk that the sample is damaged before the low dose tilt series is acquired; in this case a new sample containing the same molecules of interest may be used. It is also of no special consequence if the synthetic view data set is produced before or after the 2D experimental data set is acquired.

Figure 4:
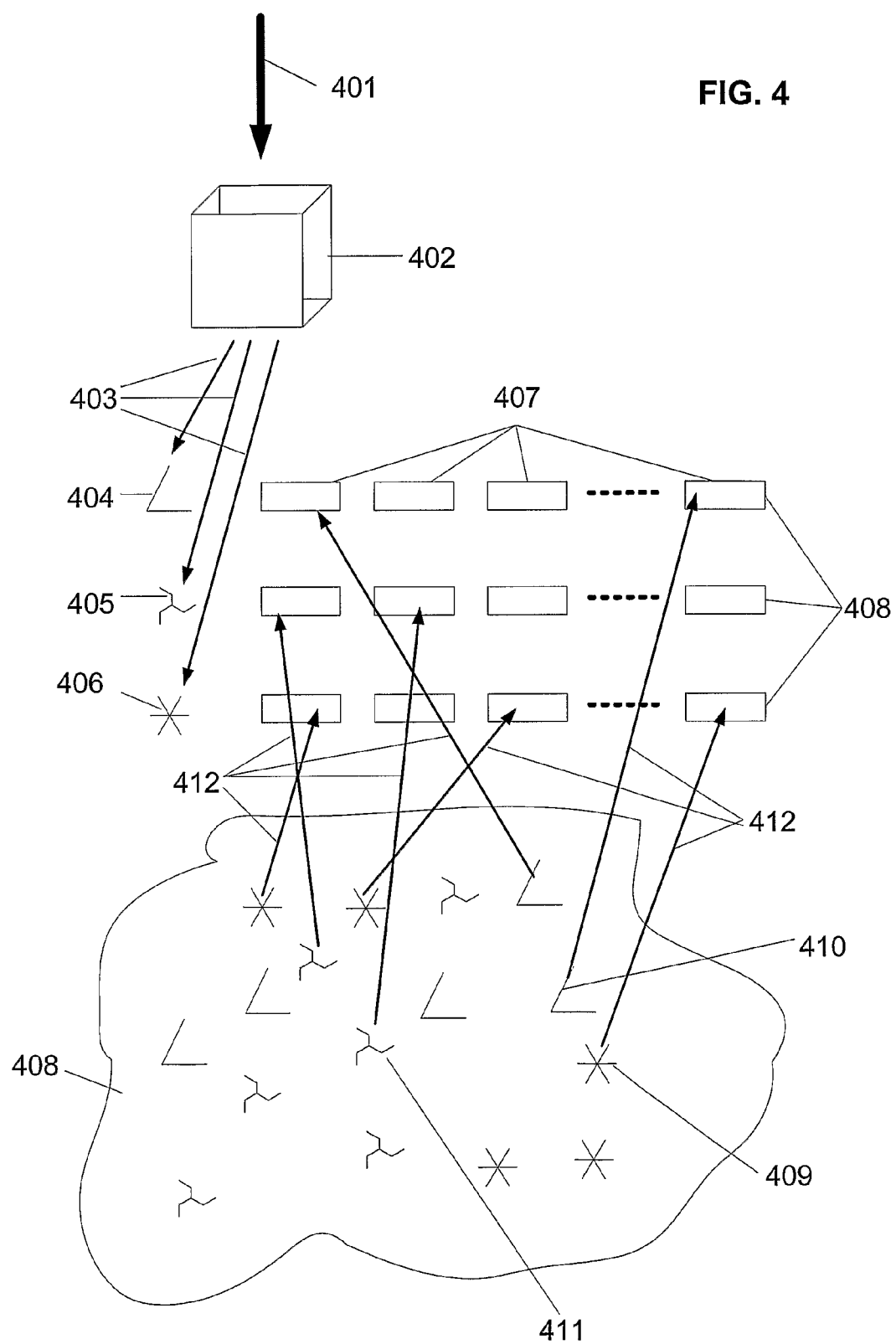
FIG. 4 illustrates schematically in a box diagram a selection process according to the present invention

FIG. 4 illustrates graphically how the method may be implemented. An electron beam 401 is exposed to a sample 402 in an electron microscope and at least one molecule or molecule conformation 404, 405, 406 of interest is measured and a 3D structure for that molecule is determined. Arrows denoted 403 illustrates graphically that at least one conformation is found from the sample. For each molecule of interest a set of different 2D synthetically image representation data sets 408 are produced for different view points and microscope configurations; each row 408 of boxes indicate a particular molecule or molecule conformation and each column 407 indicate different view points and/or microscope configuration. At least one 2D high dose image 408 is acquired with the molecule or molecules 409, 410, 411 of interest present. Each molecule conformation 409, 410 411 from the 2D image is mapped or correlated 412 to corresponding 3D-2D view point representation (407, 408).

The method may be applied in several different applications such as for instance for determining available structures in a sample and available conformations of a molecule, determine statistically the number of certain molecules or molecule conformations. It may also be used for determining structure within biological tissue that is easily damaged by the electron beam present in the electron microscope.

Figure 5:
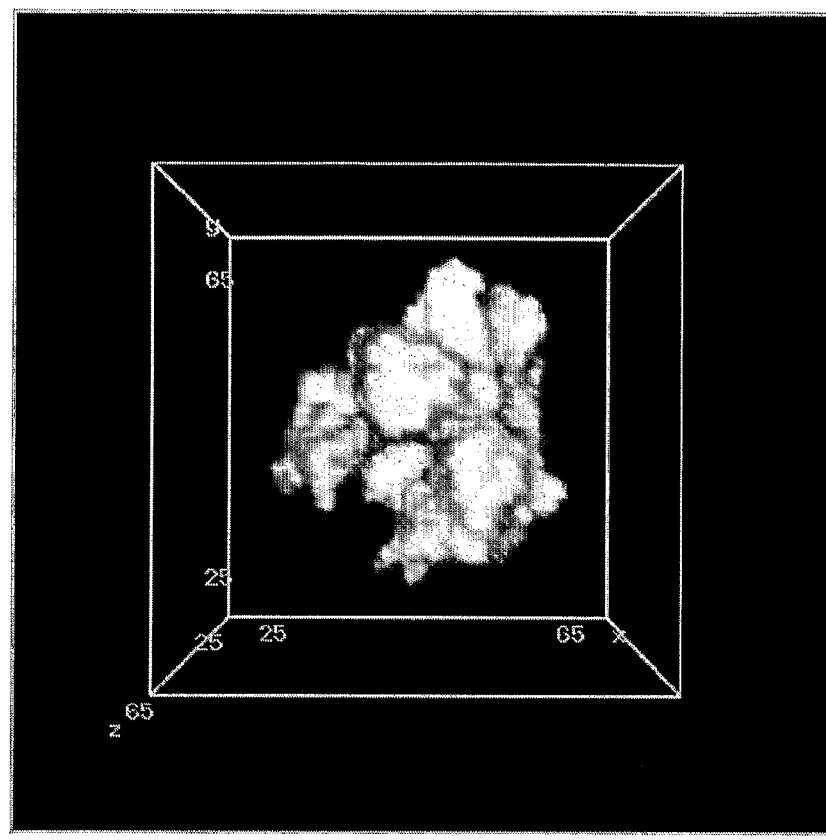
FIG. 5 shows an example using a simulated image.
Figure 5:
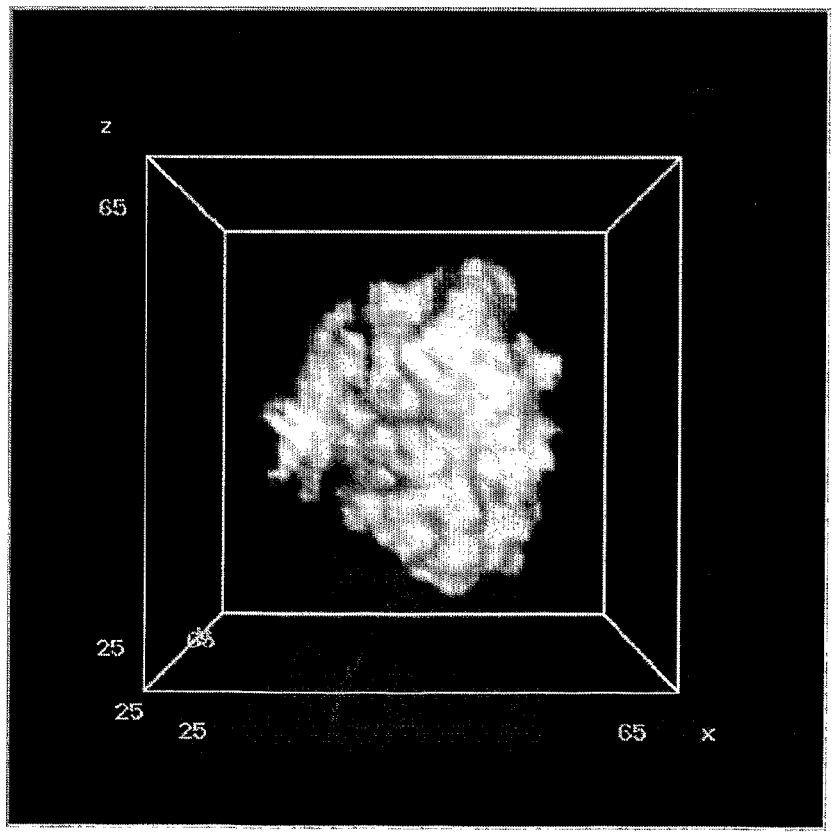

Example illustrating the effectiveness of the method according to the present invention A simulated image of RNA polymerase II was generated from the crystal structure by simulation at 10 Å resolution which is viewed from the top (left) and from the side (right) in FIG. 5. The model used for generating the images is used for generating synthetic electron tomography data instead of generating them in a microscope. However, this has no consequence for the method according to the present invention.

Figure 6:
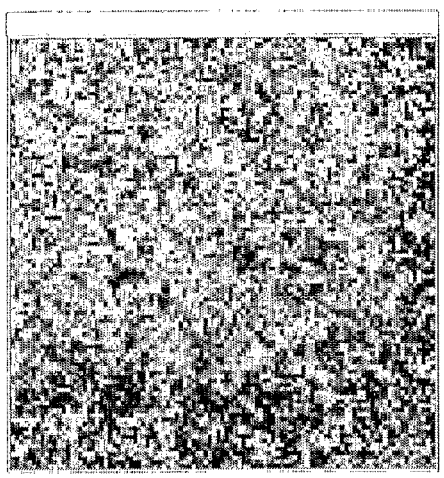
FIG. 6 shows a few images from a tilt series using the simulated image from FIG. 5.
Figure 6:
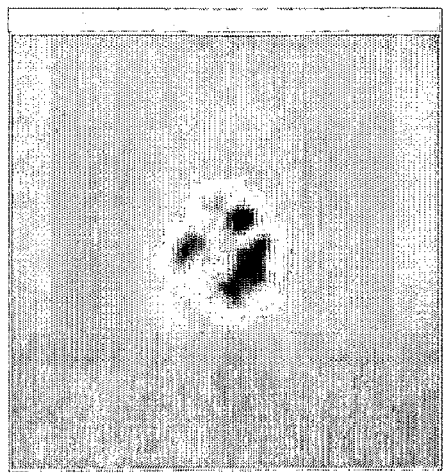
Figure 6:
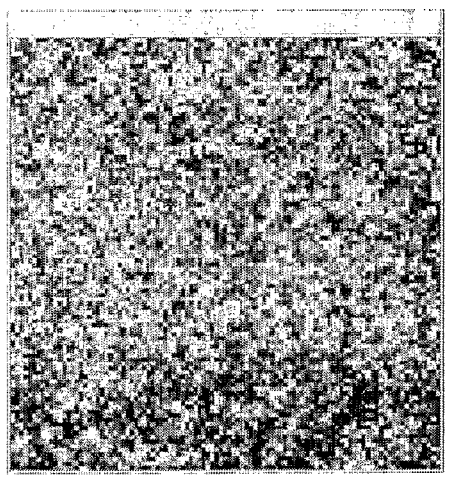
Figure 6:
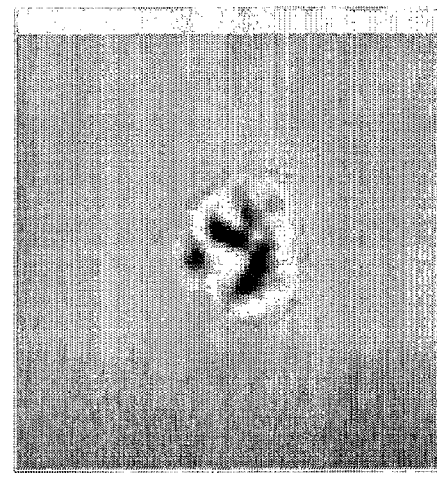
Figure 6:
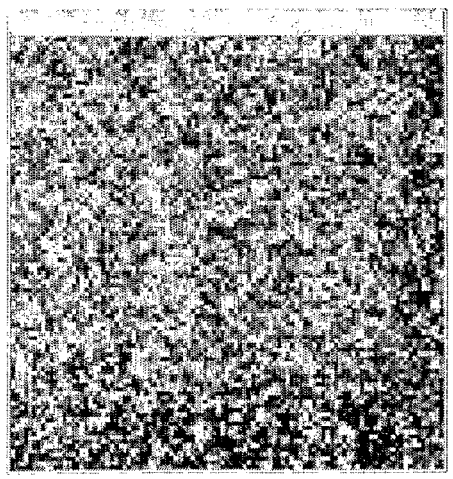
Figure 6:
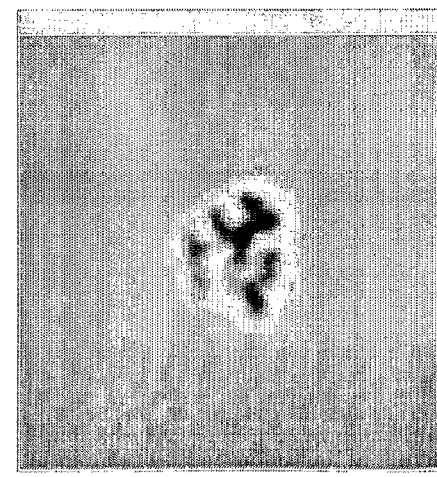

A simulated low-dose tilt series was generated with a total of 61 images, three of which can be seen in the left column of FIG. 6. The right column shows the same images without noise. A dose of 2 e/Å$^2$ for each image was used giving a total dose of 120 e/Å$^2$.

Figure 7:
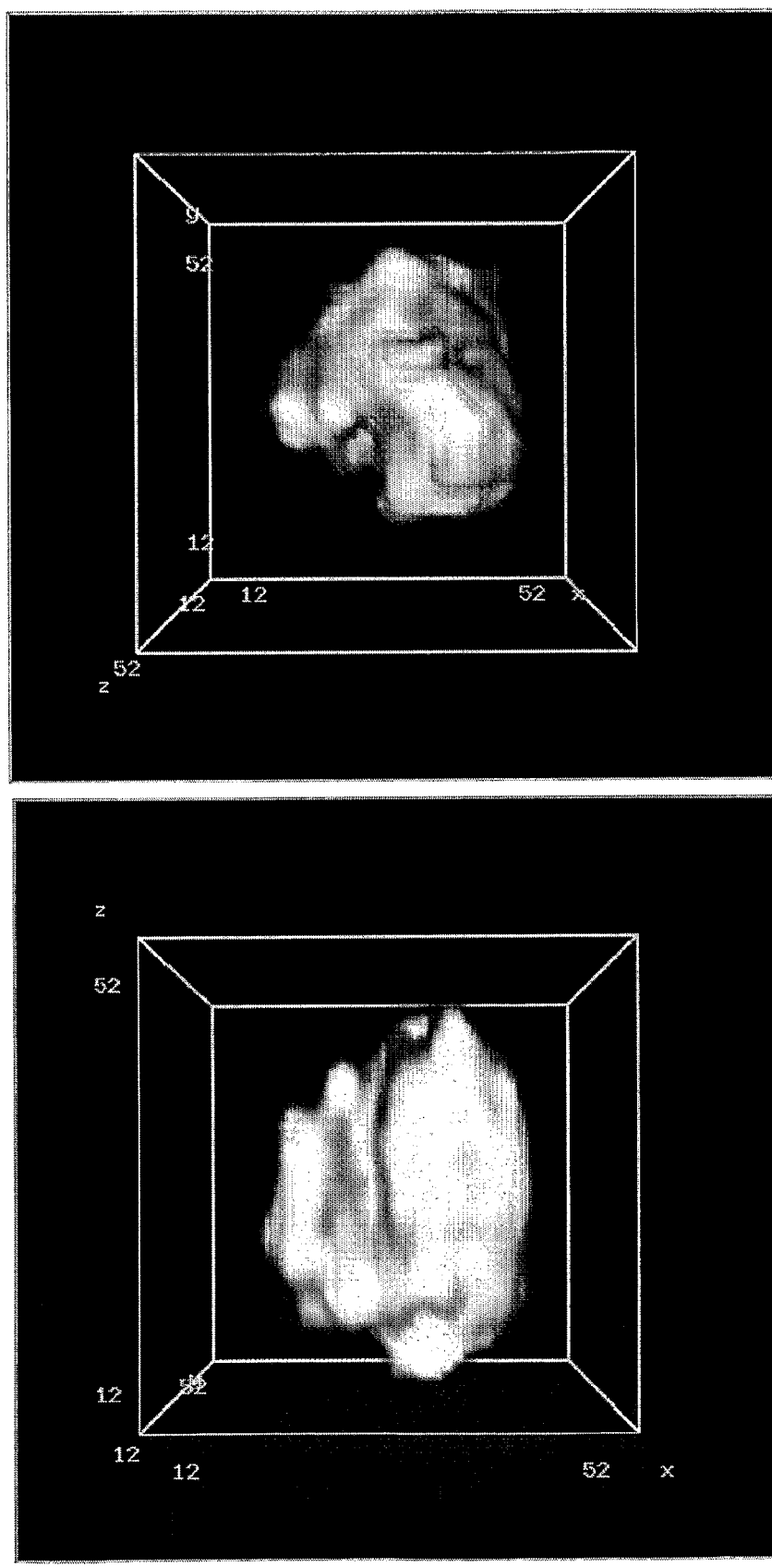
FIG. 7 shows a 3D map reconstructed from the tilt series of FIG. 6.

A three dimensional map was reconstructed from the 61 images in the low-dose tilt series viewed from the top in the left picture of FIG. 7 and from the side in the right picture. By using projections from the reconstructed low-dose tilt series objects from the high-dose series can be found. These objects can be oriented and a new reconstruction is made with all objects resulting in an improved resolution.

Figure 8:
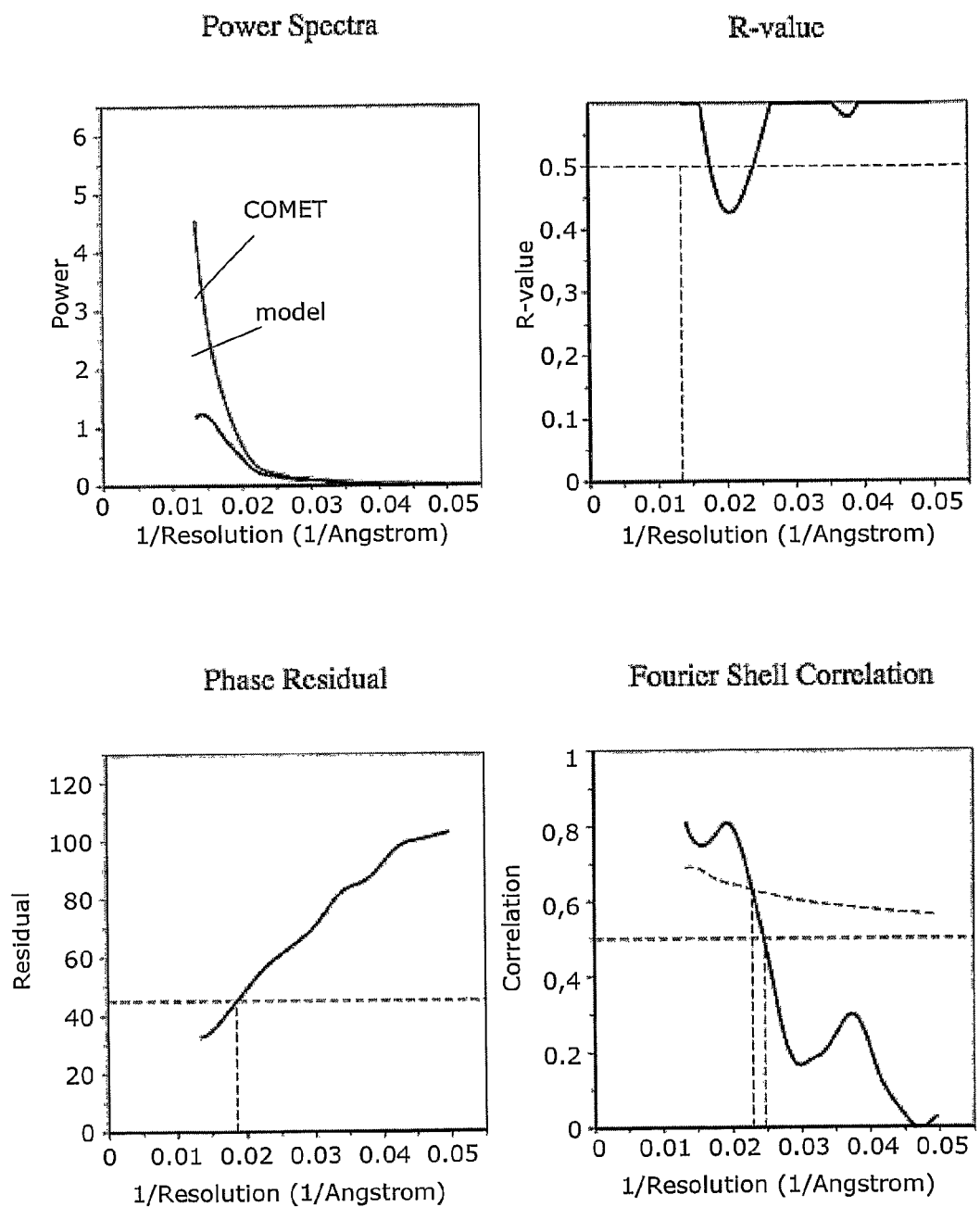
FIG. 8 shows a Fourier shell correlation between the tilt series of FIG. 6 and 3D map of FIG. 7.

FIG. 8 shows a Fourier shell correlation of the 3D map reconstructed from the low-dose tilt series versus the model map. The two maps are similar to 44 Å resolution using the 1-bit criteria and 41 Å using the 0.5-criteria. High-dose images were randomly generated using a dose of 120 e/Å$^2$ for each image without a tilt.

Figure 9:
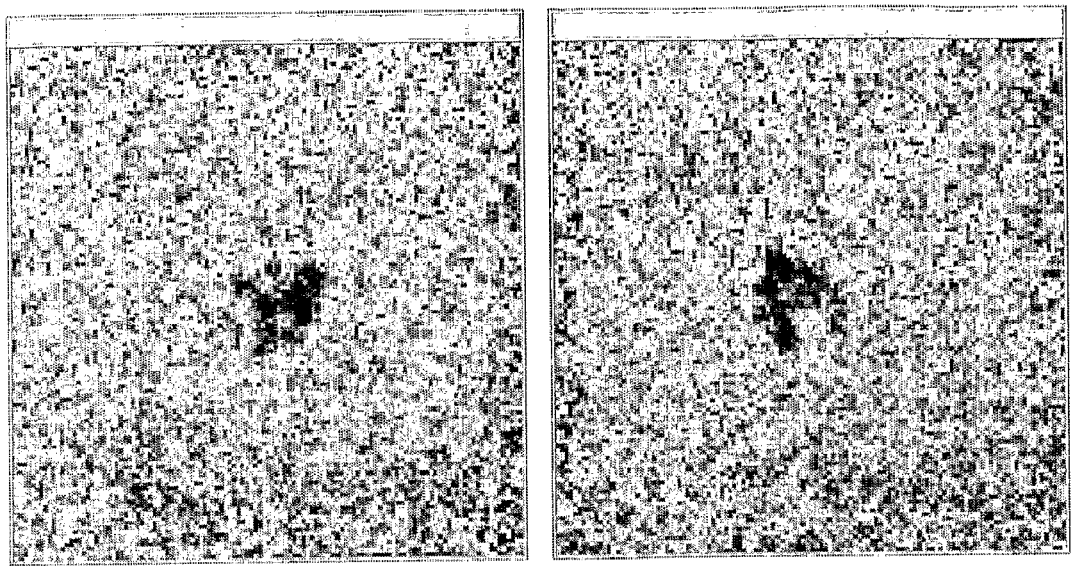
FIG. 9A shows high dose images generated in random view directions.
FIG. 9B shows two projections generated from low-dose 3D map.
Figure 9:
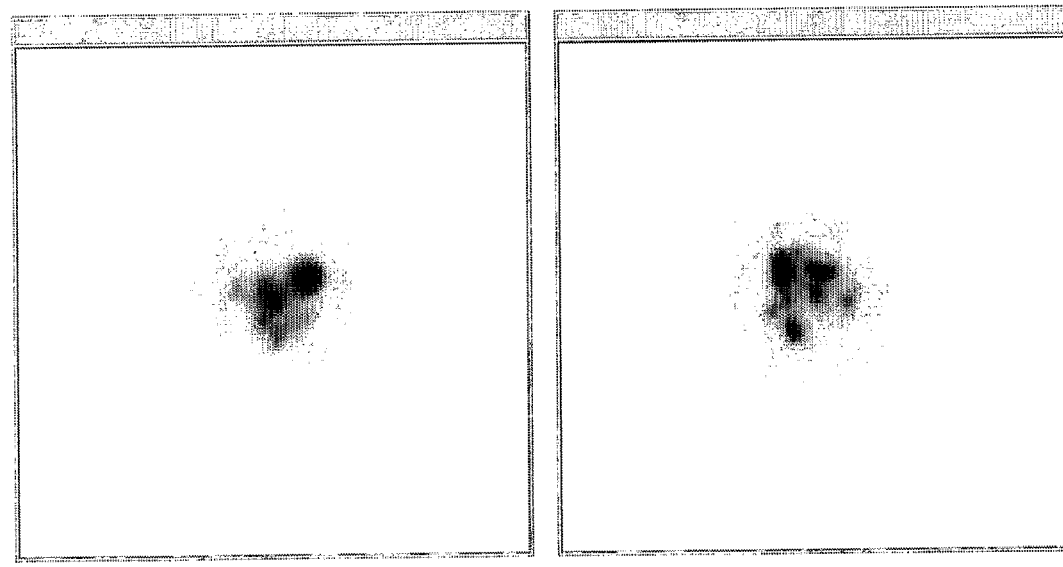

FIG. 9A shows two out of 1000 of the high-dose (120 e/Å$^2$/image) images generated without tilt. The lower pictures 9B shows two projections (out of 8000) that were generated from the low-dose 3D map in known directions from FIG. 7. These two probes were the best matches in the 2D correlation search to determine the view direction of the upper high-dose images in FIG. 9.

Thereafter a three dimensional map is reconstructed using the 3D reconstructions obtained in FIG. 7 and adding the high-dose images found in FIG. 9.

Figure 10:
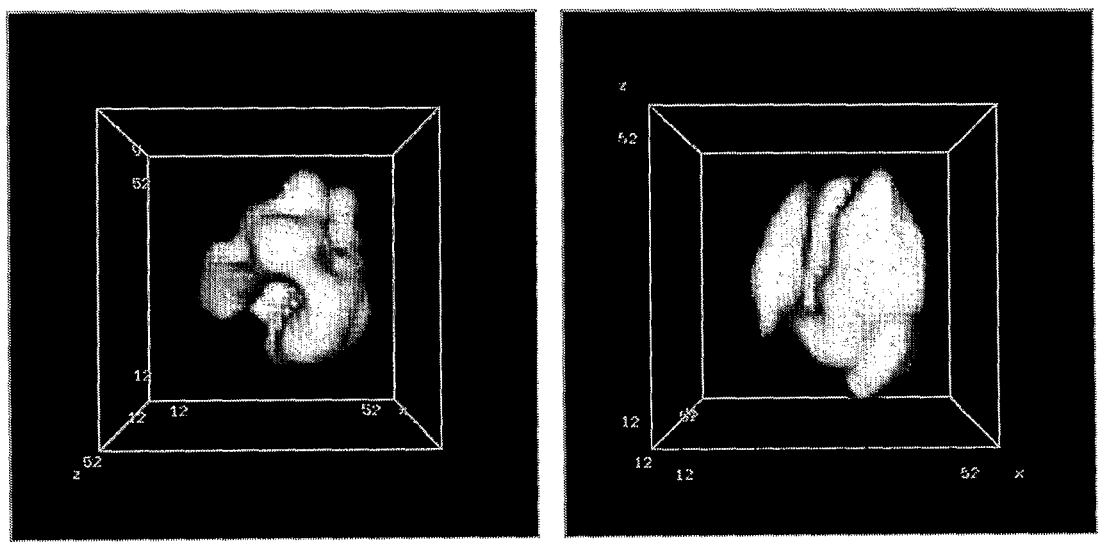
FIG. 10 shows a 3D map reconstructed from high dose images using AMET algorithm.

FIG. 10 shows such a three-dimensional map reconstructed from 571 high-dose images found in FIG. 9 which have been added to the 3D reconstructions found in FIG. 7.

Figure 11:
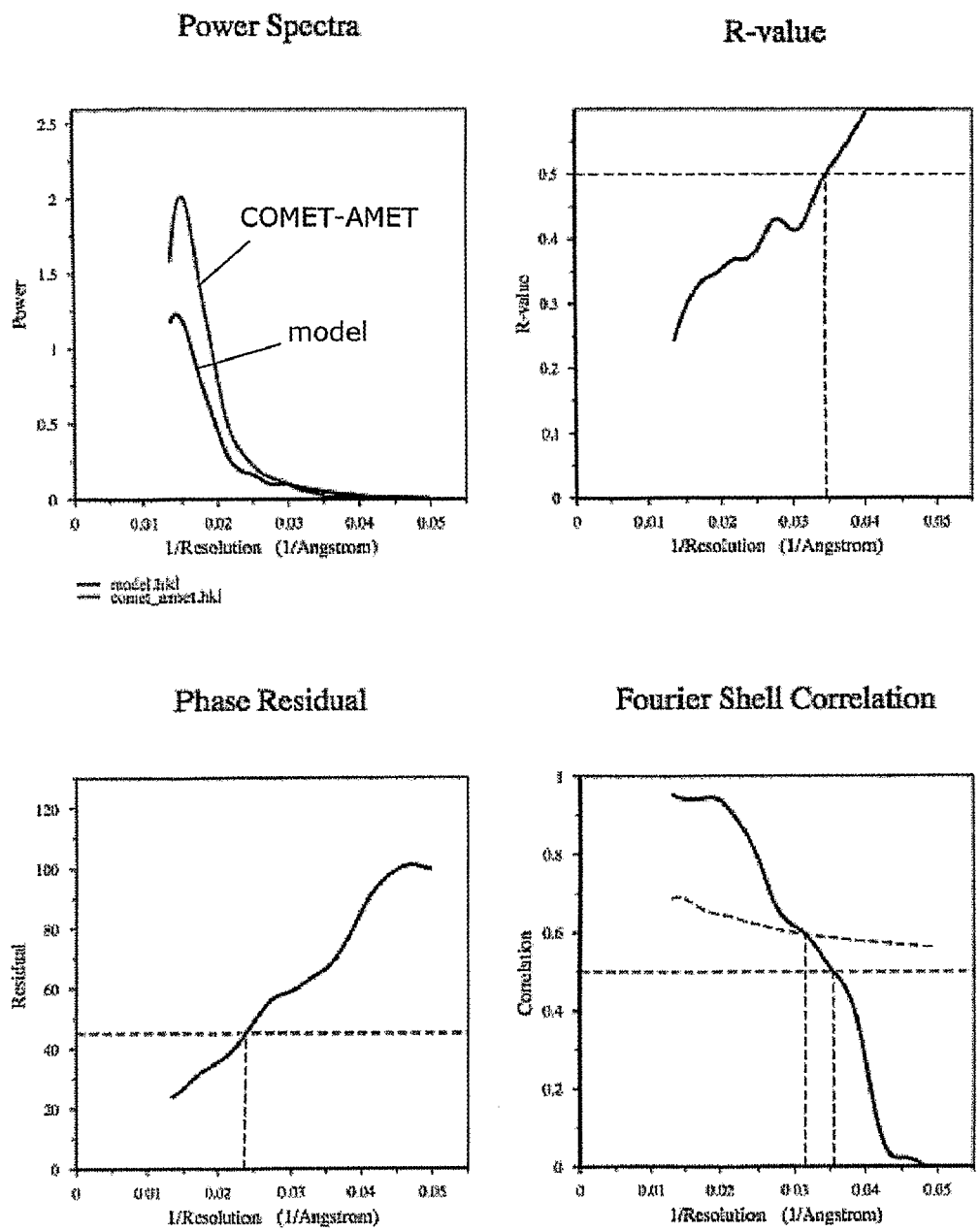
FIG. 11 shows a Fourier shell correlation between AMET and model map.

FIG. 11 finally shows a Fourier shell correlation of the 3D map reconstructed by the AMET algorithm versus the model map. The two maps are similar to 31 Å resolution using the 1-bit criteria and 28 Å using the correlation –0.5-criteria.

By using projections from reconstructions of low-dose tilt series is it possible to find objects in high dose series. These objects can thereby be oriented and then a new reconstruction can be made with all objects and one may obtain an increased resolution. In this example from 44 to 31 alternatively from 41 to 28 Å depending on which method is used for determining resolution.

It should be noted that the word "comprising" does not exclude the presence of other elements or steps than those listed and the words "a" or "an" preceding an element do not exclude the presence of a plurality of such elements. It should further be noted that any reference signs do not limit the scope of the claims, that the invention may be implemented in part by means of both hardware and software, and that several "means", "devices", and "units" may be represented by the same item of hardware.

The above mentioned and described embodiments are only given as examples and should not be limiting to the present invention. Other solutions, uses, objectives, and functions within the scope of the invention as claimed in the below described patent claims should be apparent for the person skilled in the art.

The invention claimed is:

1. A method for improving image resolution of a three dimensional structure of at least one molecule conformation comprising the steps of:
   determining a three dimensional structure of at least one conformation of a molecule in a sample from a first data set obtained from a series of 2D measurements of different geometrical projections of the molecule at a low electron beam dose in an electron microscope;
   producing a second data set comprising calculated two dimensional projections of the determined three dimensional structure of the at least one conformation of the same molecule;
   correlating data from a third data set obtained from at least one measurement of the same molecule in an electron microscope using a higher electron beam dose with the second data set; and
   using the correlated data to improve the resolution of the three dimensional structure of the at least one conformation of the molecule by increasing the first data set with the correlated data and re-determining a three dimensional structure.

2. The method according to claim 1, wherein said low dose electron beam is below a damaging level for said molecule conformation.

3. The method according to claim 1, wherein said low dose electron beam is below 1 e$^-$/Å$^2$ per image.

4. The method according to claim 1, wherein said higher dose electron beam is higher than 1 e$^-$/Å$^2$ per image.

5. The method according to claim 1, wherein said step of determining a three dimensional structure comprise a step of using a non-iterative method such as filtered back projection.

6. The method according to claim 1, wherein said step of determining a three dimensional structure comprise a step of using an iterative method such as constrained maximum entropy tomography method.

7. The method according to claim 1, wherein said step of determining a three dimensional structure comprise a step of using a combination of a non-iterative method and an iterative method.

8. The method according to claim 1, further comprising the step of producing a new second data set by simulating two dimensional projections of said improved three dimensional structure.

9. A machine with a memory containing data representing a three dimensional structure obtained from the method according to claim 1.

10. A propagated signal comprising a data structure representing a three dimensional structure obtained from a method according to claim 1.

11. A computer readable data medium containing a data structure representing a three dimensional structure obtained from a method according to claim 1.

12. The computer readable data medium according to claim 11, wherein said data medium is at least one of a hard disk, diskette, CD-ROM (Compact Disk-Read Only Memory), DVD (Digital Video Disk), flash or similar removable memory media (e.g. compactflash, SD secure digital, memorystick, miniSD, MMC multimediacard, smartmedia, transflash, XD), HD-DVD (High Definition DVD), or Bluray DVD, USB (Universal Serial Bus) based removable memory media, magnetic tape media, optical storage media, magneto-optical media, and bubble memory.

13. An image stored as a data structure in a computer readable medium representing a three dimensional structure obtained from a method according to claim 1.

14. A computer program for improving image resolution of a three dimensional structure of at least one molecule conformation comprising instruction sets for:
- determining a three dimensional structure of at least one conformation of a molecule in a sample from a first data set obtained from a series of 2D measurements of different geometrical projections of the molecule at a low electron beam dose in an electron microscope;
- producing a second data set comprising calculated two dimensional projections of the determined three dimensional structure of the at least one conformation of the same molecule;
- correlating data from a third data set obtained from at least one measurement of the same molecule in an electron microscope using a higher electron beam dose with the second data set; and
- using the correlated data to improve the resolution of the three dimensional structure of the at least one conformation of the molecule by increasing the first data set with the correlated data and re-determining a three dimensional structure.

15. The computer program according to claim 14, further comprising an instruction set for producing a new second data set by simulating two dimensional views of said improved three dimensional structure.

16. An electron microscope system arranged with image analysis software for improving image resolution of a three dimensional structure of at least one molecule conformation comprising instruction sets for:
- determining a three dimensional structure of at least one conformation of a molecule in a sample from a first data set obtained from a series of 2D measurements of different geometrical projections of the molecule at a low electron beam dose in an electron microscope;
- producing a second data set comprising calculated two dimensional projections of the determined three dimensional structure of the at least one conformation of the same molecule;
- correlating data from a third data set obtained from at least one measurement of the same molecule in an electron microscope using a higher electron beam dose with the second data set; and
- using the correlated data to improve the resolution of the three dimensional structure of the at least one conformation of the molecule by increasing the first data set with the correlated data and re-determining a three dimensional structure.

\* \* \* \* \*